United States Patent
Bodewadt et al.

(10) Patent No.: US 9,259,227 B2
(45) Date of Patent: Feb. 16, 2016

(54) VASCULAR PLUG

(71) Applicant: COOK MEDICAL TECHNOLOGIES LLC, Bloomington, IN (US)

(72) Inventors: Tue Thuren Bodewadt, Solroed Strand (DK); Christina Rauff Hansen, Copenhagen (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 272 days.

(21) Appl. No.: 13/803,504

(22) Filed: Mar. 14, 2013

(65) Prior Publication Data

US 2014/0207172 A1    Jul. 24, 2014

(51) Int. Cl.
*A61B 17/00* (2006.01)
*A61B 17/12* (2006.01)

(52) U.S. Cl.
CPC ..... *A61B 17/12109* (2013.01); *A61B 17/12136* (2013.01)

(58) Field of Classification Search
CPC .............. A61B 2017/00557; A61B 17/1671; A61B 17/1697; A61B 17/1757; A61B 17/1796; A61B 17/60; A61B 17/7002; A61B 17/7008; A61B 17/864; A61B 17/7001; A61B 17/7049; A61B 17/7013; A61B 17/7097; A61M 2025/1093; A61M 25/0017; A61M 25/10185; A61M 25/1018; A61M 2025/0018; A61M 2025/1052; A61M 2025/1054; A61M 2025/1072; A61M 2202/0496; A61M 25/04; A61M 25/10; A61M 25/10186
USPC ............................. 606/99, 105, 106; 604/500
See application file for complete search history.

(56) References Cited

U.S. PATENT DOCUMENTS

| 4,364,392 | A  | * | 12/1982 | Strother et al. ............... 606/195 |
| 6,638,293 | B1 |   | 10/2003 | Makower et al. |
| 6,706,051 | B2 | * | 3/2004  | Hudson et al. ................ 606/196 |
| 6,964,667 | B2 | * | 11/2005 | Shaolian et al. ................ 606/99 |
| 8,480,647 | B2 | * | 7/2013  | Shohat et al. ................ 604/500 |
| 2008/0045996 | A1 |  | 2/2008 | Makower et al. |
| 2008/0221600 | A1 |  | 9/2008 | Dieck et al. |

FOREIGN PATENT DOCUMENTS

WO   WO 2008/022327 A2   2/2008
WO   WO 2011/154828 A2  12/2011

OTHER PUBLICATIONS

Great Britain Combined Search and Examination Report under Sections 17 and 18(3) for GB1300930.3, mailed Apr. 25, 2013.

* cited by examiner

*Primary Examiner* — Michael Brown
(74) *Attorney, Agent, or Firm* — Brinks Gilson & Lione

(57) ABSTRACT

A vascular plug for implantation into a patient's vessel includes an inflatable balloon and a flow accelerator. The flow accelerator includes a conical portion and a tubular coupling element which couples the conical portion to an aperture to the interior of the inflatable balloon. The flow accelerator will concentrate and therefore accelerate fluid flow into the inflatable balloon. Flow accelerator will increase the pressure of fluid thereby to cause the inflatable balloon to inflate even within a pressurised blood vessel. The plug may include a sleeve which provides a chamber between the flow accelerator and the balloon, into which blood may pass from the inflatable balloon or the flow accelerator to create additional blood statis and as a result thrombosis and a second occlusive barrier.

9 Claims, 4 Drawing Sheets

VASCULAR PLUG

CROSS-REFERENCE TO RELATED APPLICATIONS

This application is related to and claims the benefit of priority to GB 1300930.3, filed on Jan. 18, 2013 which is incorporated herein by reference in its entirety.

TECHNICAL FIELD

The present invention relates to a vascular plug or occluder for closing a body vessel.

BACKGROUND ART

Vascular occluders have been known for a number of years. Many types are in the form of a device which is implanted within a vessel of the patient and which has a structure which closes off the vessel so as to occlude blood flow. Occluders of this nature, sometimes referred to as vascular plugs, are preferable over more traditional forms of occluder, such as vascular constrictors, which generally require an invasive medical procedure. Vascular occluders, on the other hand, can be deployed endoluminally in a significantly faster and less traumatic medical procedure.

Vascular occluders may be designed or used to provide temporary occlusion, for example to be effective only for the duration of a medical procedure or during a period of treatment. Occlusion may also be permanent, in which case the occluder will be left within the patient indefinitely.

There are generally two types of vascular occluders. The first type promotes embolization within the vessel, for instance by slowing the flow of blood through the device and in some cases with the addition of embolization promoters. Such devices do not produce immediate occlusion of the vessel as they rely upon the formation of sufficient blood clotting to act as the occluding barrier. Sufficient thrombosis can take hours, days or even weeks in some instances.

Another type of vascular occluder has an impervious element, typically a membrane, attached to a supporting structure which gives it a conical shape. The wide end of the device expands to spread across the entire diameter of the vessel and thus creates an instantaneous barrier to blood flow. Other examples provide an inflatable balloon or chamber, which is filled with fluid to expand the balloon or chamber and thereby cause it to fill the diameter of the vessel in which the balloon or chamber is placed, thereby closing off the vessel. In many cases immediate occlusion of this type is preferable. However, some designs of such occluders do not reliably counter the full force of the blood stream, leading to migration of the device, loss of positional orientation, failure to achieve a full seal against the vessel wall and thus failure of the device. Furthermore, some such devices can fail to deploy properly in the vessel, leading to them being ineffective from the start.

In addition to difficulties in accurate placement and risk of migration, an occluder may also leak or become dislodged if the vessel changes size or shape over time. Such size or shape change can lead to loss of connection to the vessel wall.

Some examples of known vascular occluders can be found in U.S. Pat. No. 6,638,293 and US-2008/0221600.

BRIEF DESCRIPTION OF THE INVENTION

The present invention seeks to provide an improved vascular plug or occluder. The preferred embodiments provide an occluder of which at least a part is impervious so as to create substantially immediate occlusion of a vessel. In some embodiments, the vascular occluder also includes a permeable element designed to provide a region of stagnant blood to promote embolization.

According to an aspect of the present invention, there is provided a vascular plug for occluding a body vessel, the plug including an inflatable element provided with an aperture, and a flow accelerator including first and second ends, the first end providing a greater flow area than a flow area of the second end, the second end being coupled to the aperture of the inflatable element.

This structure provides an inflatable device, for instance a balloon, which when inflated can close off a vessel so as to occlude it. The flow accelerator has the effect of increasing the fluid flow and thus pressure thereof into the inflatable member. This can enable the chamber to be inflated by the blood stream alone without the need for a separate inflation mechanism. Moreover, the structure can allow for the inflatable element to be continually subjected to inflation pressure, through the flow accelerator, thereby to expand with any expansion of the vessel, thereby to maintain reliable occlusion of the vessel.

In the preferred embodiment, the flow accelerator, or concentrator, is conical. In another embodiment, the flow accelerator includes a conical portion and preferably a cylindrical portion attached to the first end of the conical portion.

In the preferred embodiment, the device includes a one-way valve at the aperture of the inflatable element. Some embodiments can have a permanently open aperture to the inflatable element, relying on constant pressure from the patient's blood stream pressure to keep the inflatable element under pressure. However, it is preferred that there is provided a one-way valve, which maintains fluid and thus pressure inside the inflatable element and therefore maintains the element's inflated diameter even when there is a drop off in blood pressure, for example once thrombosis has occurred upstream of the vascular plug, between heat beats, during fluid back flow and so on. It will be apparent that the one-way valve is configured to allow fluid into the inflatable member and to block fluid flow out of the inflatable member.

The second end of the flow accelerator provides or includes a neck, which may include a tubular neck section. A coil may be provided in the neck section, advantageously having an internal coil surface providing a threaded coupling. The coil can provide a coupling thread for a delivery detach mechanism, providing a convenient and reliable deployment structure for the plug.

At least one of the inflatable element and the flow accelerator may be made of an expandable or elastic material. In another embodiment, at least one of the inflatable element and the flow accelerator is made of an inextensible material.

The inflatable element and/or the flow accelerator is made of a material from the group including: polyurethane, polyamide, polyether block amide, silicone and thermoplastic elastomers.

Use of an expandable or elastic material for the inflatable element and/or flow accelerator enables the device to attain a fully deployed configuration over a range of diameters, in contrast with devices made of non-elastic material which may remain only partially deployed, in particular to be partly folded when in situ. An expandable or elastic inflatable element can apply a constant force against the vessel wall, thereby ensuring good patency and a good grip to the vessel wall. It is not always practicable to match a device size precisely to a vessel diameter, at least for the reasons given above.

Advantageously, there may be provided a sleeve disposed outside of and between the first end of the flow accelerator and the inflatable member. The sleeve preferably provides a fillable chamber. In practice, the chamber may be blood fillable, to store stagnant blood which will tend to coagulate into a thrombus and therefore provide an additional occluding barrier. In this regard, there may be provided one or more fluid outlets in the inflatable element coupling into the fillable chamber, thereby to pass blood from the inflatable element into the cylindrical chamber.

In another embodiment, there may be provided a generally conical fillable chamber around the flow accelerator, which may take the form of a closed conical membrane disposed radially outside of the flow accelerator. Such a chamber can provide a support structure, formed by filling the space between the flow accelerator and the membrane with blood. The blood will over time coagulate within the chamber, thereby to provide in effect a thickening and strengthening of the wall of the flow accelerator.

In an embodiment, the flow accelerator is at least partially permeable.

There may be provided one or more fluid outlets in the inflatable element. Advantageously, the one or more fluid outlets are disposed in a part of the inflatable element which faces upstream, in practice in a part of the inflatable member facing the flow accelerator. In this embodiment, the device may include, as previously explained, a sleeve coupling an outer perimeter of the flow accelerator with an outer perimeter of the inflatable member to create a chamber between the inflatable member and the flow accelerator, the one or more outlets connecting the interior of the inflatable element to the chamber. With this structure, it is not necessary for there to be a passage for blood from an upstream direction, typically from the flow accelerator. The outlet or outlets will assist in the creation of a volume of static blood in the device and thus in the promotion of thrombosis.

In an embodiment, the device may include two flow accelerators in opposing relationship either side of the inflatable member, both flow accelerators being coupled to a respective aperture in the inflatable member. Such a two way plug may be filled from either side. Advantageously, the inflatable member includes a one-way valve at each aperture.

Preferably, the inflatable member has a diameter which is greater than its length.

According to another aspect of the present invention, there is provided a method of occluding a body vessel, including the steps of:

providing a vascular plug, the vascular plug including an inflatable element provided with an aperture; and a flow accelerator including first and second ends, the first end providing a greater flow area than a flow area of the second end, the second end being coupled to the aperture of the inflatable element;

locating the vascular plug in a body vessel with the first end of the flow accelerator facing a direction of fluid flow such that fluid from the fluid flow enters the flow accelerator and thereby to cause inflation of the inflatable element and occlusion of the body vessel.

In the case where the vascular plug includes opposing flow accelerators, the method includes the step of placing the vascular plug in a body vessel such that the first end of one of the flow accelerators faces the blood flow. The first end of the other flow accelerator would thus face downstream of the blood flow.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
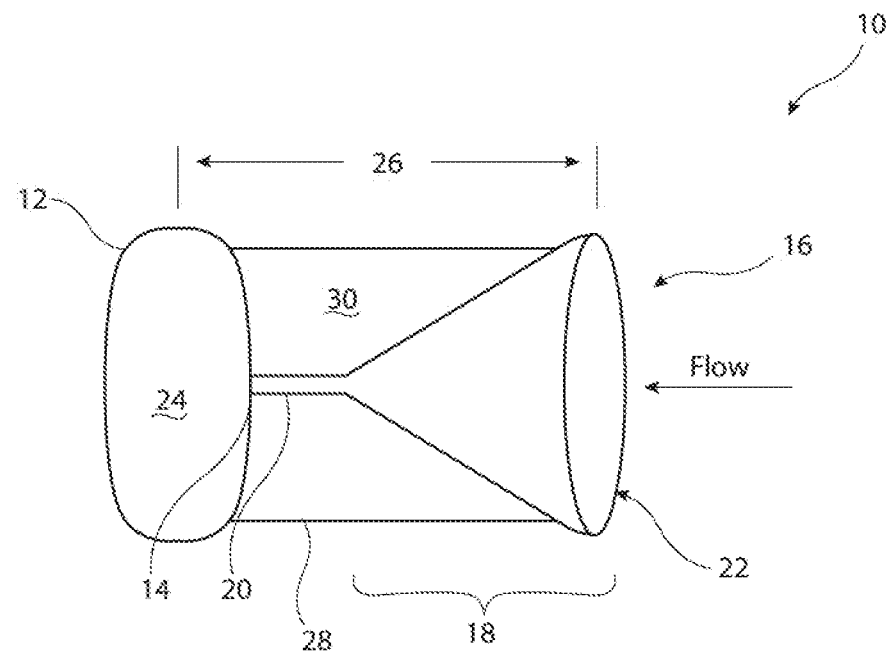
FIG. 1 is a side elevational view first embodiment of vascular plug.

Referring to FIG. 1, there is shown a first embodiment of plug 10 according to the present invention. The view shown is a side elevational view in partial cross-section. The plug includes an inflatable element 12 which could be described as a balloon, which may be made of conventional balloon material such as polyurethane, polyamide such as Nylon, polyether block amide such as Pebax, or any other suitable material. In the preferred embodiment, the material of the inflatable element 12 is an expandable or elastic material such as silicone or a thermoplastic elastomer.

The inflatable element 12 is in transverse cross-section, in practice perpendicular to the vessel and direction of fluid flow as shown by the arrow in FIG. 1, generally circular so as to have a shape consistent with the cross-sectional shape of the vessel. The inflatable member element 12 may have a transverse diameter, normal to the direction of flow, which is greater than its length, as can be seen in FIG. 1. In other embodiments, though, the inflatable element 12 may be longer and may, for instance, be longer than it is wide.

The inflatable element 12 has at least one aperture 14 which is connected to an end of a flow accelerator 16. In this embodiment, the flow accelerator 16 has a conical portion 18, which serves to concentrate and accelerate flow of fluid along its length. A tubular connector portion 20 fluidically connects the narrow end of the conical portion 18 of the flow accelerator to the aperture 14 in the inflatable element 12. Typically, the aperture 14 will be substantially round and located at the centreline or close to the centreline of the device 10 and thus of the radial and axial centre of the inflatable element 12

The flow accelerator 16 has, in the preferred embodiment, a round wide end 22 and is round in transverse across-section for the whole of its length to its narrow end, although it is not essential that it is entirely round. The structure is such that there is a direct flow path from the wide end 22 of the flow accelerator 16 into the interior chamber 24 of the inflatable element 12.

The flow concentrator 16, including the conical portion 18 and the tubular connector 20, are preferably made of the same material as the inflatable element 12 but may be made of a different material. In the preferred embodiment, the inflatable element 12 and the flow concentrator 16 are made of impermeable materials, but it is not excluded that one or both may be partially permeable, as described below.

It will be appreciated that the tubular connector 20 is not a necessary component of the structure of plug 10 shown in FIG. 1, as the narrower end of the conical portion 18 of the flow accelerator 16 could be coupled directly to the aperture 14 of the inflatable element 12.

The plug 10 is designed to be disposed in a patient's vessel with the wide end 22 of the flow accelerator 16 facing upstream so as to be opposite the direction of fluid flow and the inflatable element 12 downstream of this. Both the edges of the wide end 22 of the flow accelerator 16 and the circumferential periphery of the inflatable element 12 will be in contact with the vessel wall.

It will be appreciated that the longitudinal separation 26 between the wide end 22 of the flow accelerator 16 and the point of greatest diameter of the inflatable element 12 (its circumferential periphery) creates two spaced contact and support points for the plug 10 within the vessel. These support points assist in maintaining the plug 10 correctly oriented and in position in the vessel, and minimise the risk of the plug 10 tilting in the vessel, as can occur with prior art plug structures.

Once located in a vessel, fluid flowing towards the plug 10 will pass into the flow accelerator 16 and accelerate as a result of the taper of the conical portion 18, until it eventually passes through the tubular connector 20 and into the inflatable element 12. The increase of the flow speed will create an effective increase in fluid pressure leading into the inflatable element 12, thereby causing the element 12 to inflate. Continued pressure of blood flow in the patient's vessel will continue to urge blood into the flow accelerator 16 and thus into the inflatable element 12. This keeps the inflatable element 12 in an inflated condition and also acts to cause this to expand further if there is any expansion of the vessel over time. The structure therefore provides a self-deploying plug assembly which can maintain a continuous expansion pressure of the inflatable element 12 against the vessel wall in order to retain the plug 10 in position and properly sealed to the vessel wall.

The flow accelerator 16 may be provided with strengthening elements (not shown) which may be in the form of a frame of resilient material, for instance a shape memory alloy such as Nitinol. The frame will assist in the deployment of the flow accelerator 16 and help hold the shape of the flow accelerator 16 when in situ.

The plug 10, and in particular the inflatable element 12 and the flow accelerator 16, are compressible, typically by wrapping and folding, so they can be delivered by a conventional introducer assembly endoluminally through the vasculature of a patient. In practice the device 10 would be radially compressed often by wrapping on to a carrier and then disposed within a sheath or catheter of an introducer assembly for deployment in a patient. Once released from the introducer assembly, the plug 10 will expand, often both as a result of the resilient nature of the materials used for the plug 10 and also as a result of the pressure of blood within the patient's vessel.

Also shown in FIG. 1 is an optional sleeve 28 which extends, in this embodiment, from the wide end 22 of the conical portion 18 of the flow accelerator 16 to the inflatable element 12, adjacent to the point of widest perimeter or radius thereof. Typically, the sleeve 28 will be fixed to or integral with the conical portion 18 of the flow accelerator 16 and to the inflatable element 12. The sleeve 28, which is generally cylindrical and round in transverse cross-section, may be made of the same material as the inflatable element 12 but could be formed of other materials, whether impervious or permeable.

The sleeve 28 creates a chamber 30 between the inflatable element 12 and the flow accelerator 16, within the longitudinal extent of the plug 10. The chamber 30 is designed to hold substantially stagnant blood therein, which in the course of time will clot to create a thrombus, acting as an additional occlusive barrier. Blood can be made to pass into the chamber 30 in a number of ways, such as by one or more holes within the wall of the flow accelerator 16, one or more holes within the wall of the inflatable element 12, which holes couple directly into the chamber 30. In another embodiment, at least a part of flow accelerator 16 is made of a porous or substantially porous material, of porosity substantially less than the expected flow of blood, thereby to ensure that the accelerator 16 still concentrates and accelerates fluid into the inflatable element 12 while providing for some fluid to pass into the chamber 30.

Figure 2:
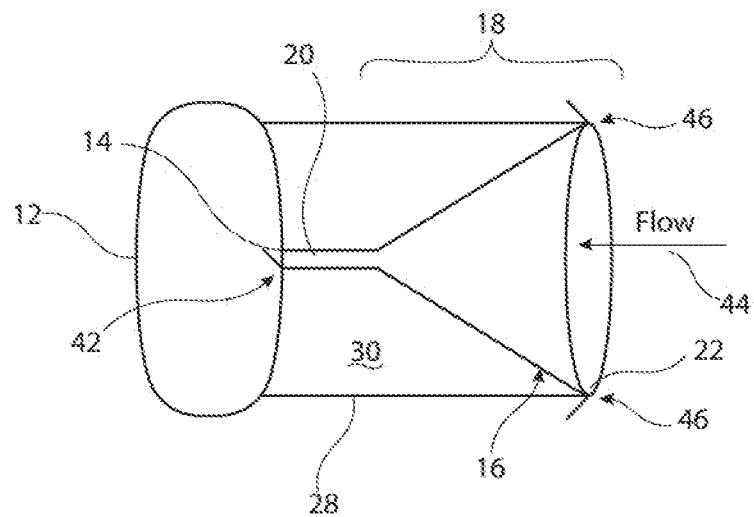
FIG. 2 is a longitudinal cross-sectional view another embodiment of vascular plug.

Referring now to FIG. 2, there is shown another embodiment of plug 40, generally very similar to the embodiment of plug 10 shown in FIG. 1. The plug 40, as the embodiment of FIG. 1, includes an inflatable element 12, a flow accelerator 16 including a conical portion 18 and a tubular connector 20, as well as a sleeve 28 providing a chamber 30 between the flow accelerator 16 and the inflatable chamber 12. As the embodiment of FIG. 1, the sleeve 28 and tubular connector 20 are preferable but not necessary.

In the embodiment of FIG. 2, there is provided a one-way valve 42 at the aperture of the inflatable element 12. The valve 42 opens in the direction of fluid flow 44 but closes in the opposite direction, in other words opens in a direction of filling of the inflatable element 12 but closes in a direction of emptying of the inflatable element 12. Thus, the one-way valve 42 enables the inflatable element 12 to be filled and ensures it cannot be emptied. In this manner, the amount of fluid within the inflatable element 12 and therefore its size when inflated will not be reduced even upon loss of pressure of fluid from the flow accelerator 16.

This can be particularly useful when the plug 10 is to be deployed in a part of the patient's vasculature which is subject to large pressure variations and fluid back flow. The one-way valve could be provided as a part of the wall of the inflatable element 12, as part of the tubular connector 20 (or the conical portion 18 where the tubular connector 20 is not provided) or as a separate element. In its simplest form, the one-way valve can be a flap of material, possibly the same material as that of the wall of the inflatable element 12, connected to the wall of the inflatable element 12 and which has a diameter larger than the hole 14.

The embodiment of FIG. 2 also includes a series of anchoring elements 46 extending radially outwardly from the wide end 22 of the flow accelerator 16, which may be in the form of barbs. These may be substantially evenly spaced circumferentially around the wide end 22 of the flow accelerator 16. As will be appreciated from FIG. 2, the anchors 46 preferably point backwards towards the distal end of the plug 10 and in practice in the direction of fluid flow 44, thus opposite the direction of force produced by the fluid flow 44.

The anchoring elements 46 may usefully be formed as a part of the strengthening elements of a frame of the flow accelerator 16. The anchoring elements 46 assist in holding the plug 40 in position in the vessel wall and minimise the risk of migration of the plug 40 as a result of the pressure from the blood flow 44.

Instead of or in addition to anchoring elements 46, the plugs disclosed herein may be provided with other measures to reduce the risk of migration of the plug within the vessel, including, for example, texturing or roughening of the surface of the inflatable element 12 which contacts the vessel wall.

It is to be appreciated that the anchoring elements 46 and the one-way valve 42 may be provided also in the embodiment of FIG. 1 and in any of the other embodiments disclosed herein and covered by the claims.

Figure 3:
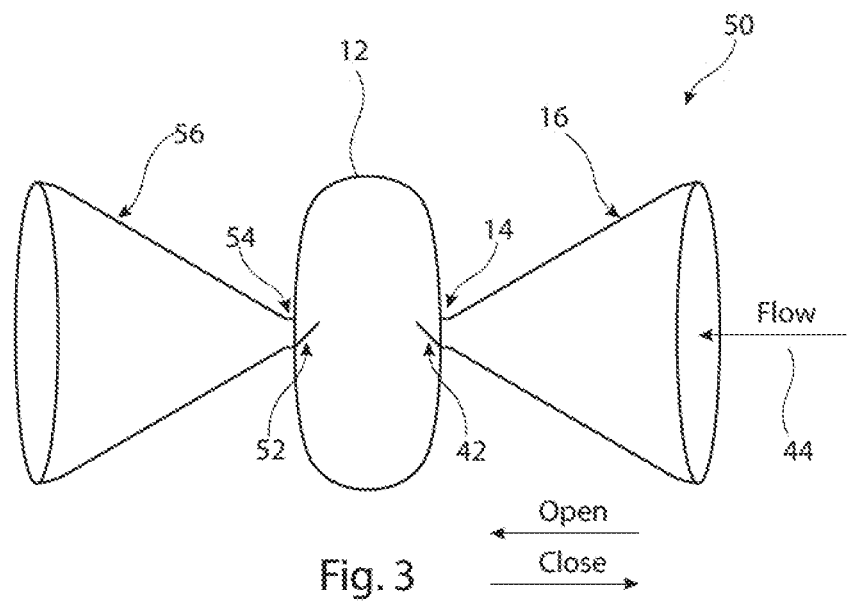
FIG. 3 is a side elevational view an embodiment of double ended vascular plug.

Referring now to FIG. 3, there is shown another embodiment of plug 50 having the general features of the embodiments of FIGS. 1 and 2, that is an inflatable element 12 coupled to a first flow accelerator 16 intended to be arranged to face the upstream direction of fluid flow 44 within a patient's vessel. The plug 50 of FIG. 3 also includes a second conical flow accelerator 56 disposed on the opposite side of the inflatable element 12 and having the same characteristics and structure of the flow accelerator 16, the only difference being its position and orientation in the device 50.

The inflatable element 12 includes a second aperture 54 which couples to the opening in the narrow end of the flow accelerator 56. Thus, the inflatable element 12 includes apertures 14, 54 both in the upstream and in the downstream direction of fluid flow 44. The plug 50 also includes first and second one-way valves 42, 52 disposed to overlie the apertures 14, 54 into the inflatable element 12. Thus, when fluid flows in the direction of arrow 44 shown in FIG. 3, the one-way valve 52 will close, whereas a one-way valve 42 open, to enable fluid to fill the inflatable element 12. On the other hand, the fluid flows in the opposite direction, that is opposite the direction of arrow 44 of FIG. 3, for example when there is back-flow of fluid within the vessel, the valve 42 will close, whereas the valve 52 will open. This reverse fluid flow will thus still contribute to filling the inflatable element 12. As a result, the inflatable element 12 of the plug 50 will be filled whatever direction fluid is flowing to the plug 50 and, similarly, whichever way the plug 50 is deployed in the vessel.

It will be appreciated that the one-way valves 42 and 52 can have the same structures and be made of the same materials.

Figure 4:
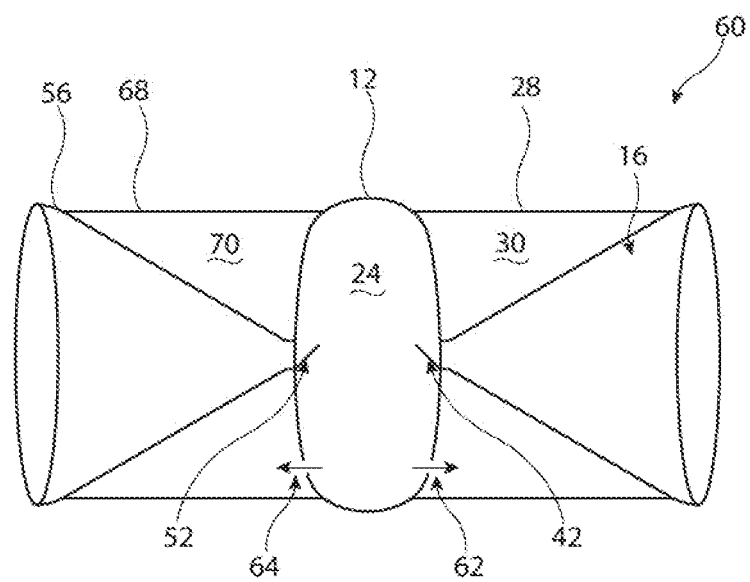
FIG. 4 is a longitudinal cross-sectional view another embodiment of double ended vascular plug.

FIG. 4 shows an embodiment of plug 60 similar in structure to the plug 50 of FIG. 3, which includes in addition first and second sleeves 28, 68 each extending between the inflatable element 12 and the wider end of its respective flow accelerator 16, 56. The sleeves 28 and 68 create two chambers 30, 70 either side of the inflatable element 12. The sleeve 68 is preferably the same structure and has the same characteristics as the sleeve 28 and as described above.

Also shown in FIG. 4 are holes 62, 64 in the wall of the inflatable element 12, which allow passage of fluid (blood) from the interior 24 of the inflatable element 12 to their respective chambers 30, 70 for filling the latter with fluid when the device 60 is implanted in a body vessel.

Thus, the embodiment of plug 60 shown in FIG. 4 can create in effect three zones of stagnant blood, namely the interior 24 of the inflatable element 12 and in the chambers 30, 70 formed by the sleeves 28, 68. It will be appreciated that these chambers, as with the other embodiments described herein, are in addition to a zone of stagnant blood which will be created within the flow accelerators 16, 56 once the inflatable element 12 has been fully inflated and allow no further flow of blood thereinto. These volumes of stagnant blood will tend to promote thrombosis and thus a creation of further occlusion barriers.

Figure 5:
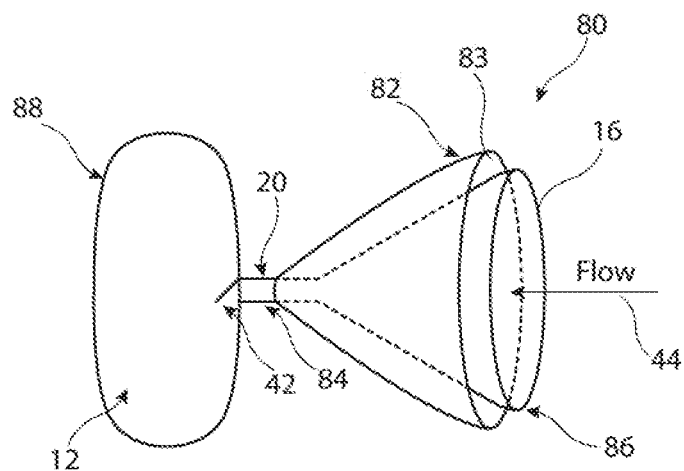
FIG. 5 is a side elevational view another embodiment of vascular plug.

Referring now to FIG. 5, there is shown another embodiment of plug 80. This embodiment has a number of elements consistent with the above-described embodiments and including, for example, the inflatable element 12, the flow accelerator 16, tubular connecting element 20 and, optionally, one-way valve 42. These elements all have the characteristics described herein.

The embodiment of plug 80 shown in FIG. 5 has in addition a second fillable element 82 which in this example is a second cone lying radially outside of and concentric with the conical portion 18 of the flow accelerator 16. The second cone 82 has an open end 83 of greater diameter than the open end 22 of the flow accelerator 16 and a closed end 84, which in this example closes around the tubular connector 20. The second cone 82 is preferably made from a similar material as that forming flow accelerator 16 and may be provided with strengthening elements such as a frame as disclosed above.

The difference in diameters at the open ends of the two cones 18 and 82 and along their lengths create an annular space 86 for receiving blood from the volume of blood within the vessel. As blood fills this space between the two cones it creates, together with the material of the walls of the cones, a self-supporting structure which presses against the vessel wall and holds the plug 80 tightly against the vessel wall. In the described embodiment, the space between the outer cone 82 and the wall of the flow accelerator 16 is sealed save for the annular aperture 86. Thus, blood will stagnate and coagulate over time to create a conical occlusive barrier which will be consistently biased open by the pressure of blood flow 44.

In the embodiment of FIG. 5, the walls of the flow accelerator 16 may be impermeable or may permeable, at least partially, in order to promote filling the space between the two cones 82, 18.

Figure 6:
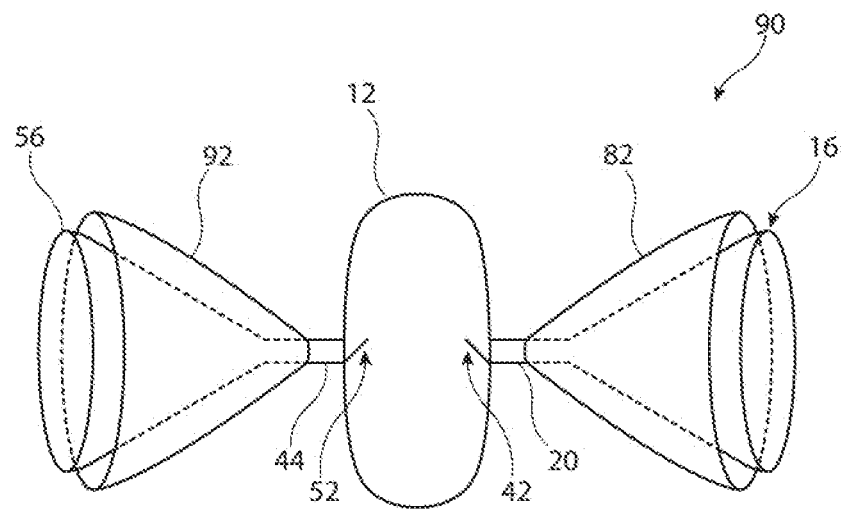
FIG. 6 is a side elevational view yet another embodiment of vascular plug.

FIG. 6 shows another embodiment of plug 90 having characteristics similar to the embodiment of FIG. 5 as well as the embodiment of FIG. 3. More specifically, the embodiment of FIG. 6 shows a double ended plug 90 similar to plug 50 of FIG. 3 but in which there is provided an additional cone 82 and 92 over each flow accelerator 16, 56, of the characteristics shown in FIG. 5 and described above. The embodiment of FIG. 6 may have all of the features of the other embodiments described herein.

It will be appreciated that the creation of a conical volume of clotted blood between the two cones 82, 18 may establish the shape of the flow accelerator 16 without the need to rely upon any sprung elements to maintain the flow accelerator 16 open.

Figure 7:
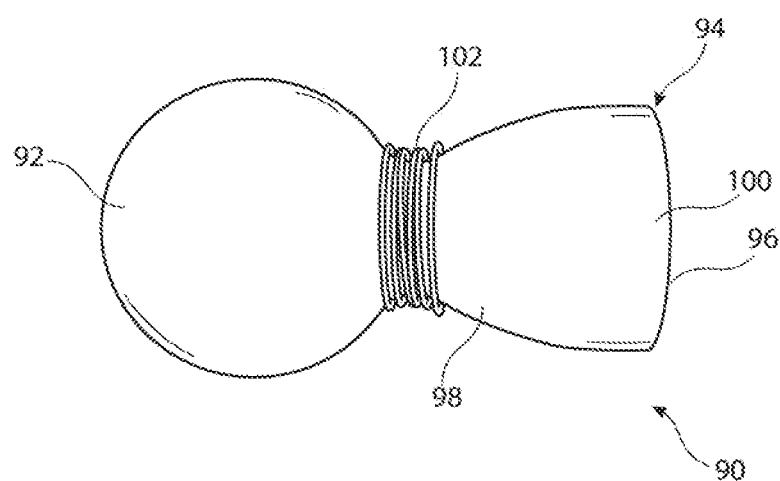
FIG. 7 is a photograph of a prototype vascular plug produced in accordance with the teachings herein.

FIG. 7 shows a photograph of a prototype vascular plug 90 produced in accordance with the teachings herein. The plug 90, which has or can have the features taught herein, includes an inflatable balloon element 92 and a flow accelerator 94 coupled to the inflatable balloon 92. The flow accelerator 94 includes a conical portion 96 and a cylindrical portion 98 extending from the wide end of the conical portion 96. The cylindrical portion helps stabilise the device 90 in a patient's lumen and improves patency of the device to the vessel walls. To optimise the fitting of the device to the vessel wall, there may be provided a stent ring 100 or other support in the cylindrical section 98, which may be provided on an internal surface of the cylindrical section 98, on an outside surface thereof or embedded in the wall thereof. Any other strengthening element may be provided.

Also shown in FIG. 7, in schematic form, is a coil 102 which in this example is disposed in the tubular section between the inflatable balloon 92 and the flow accelerator 94. The coil 102 has its internal surfaces protruding into the inside of the tubular coupling section and in practice provided a threaded connector, which can couple to a threaded detach tool of a deployment assembly. Thus, the plug 90 can be reliably connected to a deployment assembly, positioned in the desired location in a patient's vasculature and then separated form the deployment assembly by a simple unscrewing action.

With regard to deployment of the plug taught herein, in all embodiments it is envisaged that this can be achieved by means of a standard introducer assembly in which the plug is radially constrained, for example by compression and/or wrapping around a carrier element, into the sheath of an introducer assembly, for delivery endoluminally through the vasculature of a patient. Once released from the introducer assembly, the plug will expand radially outwardly against the vessel walls, with the flow accelerator filling the interior of the inflatable element 12 to cause this to create an occluding barrier and to engage itself with the vessel walls. The structure thus creates substantially immediate occlusion of a vessel and occlusion which can be maintained over time, even when the vessel changes dimensions or shape.

The interior 24 of the inflatable element 12 will create blood statis which will promote clotting, as will the other regions around the inflatable element 12 which hold blood substantially stagnant within the vessel. The device can thus produce permanent occlusion of a vessel.

The flow accelerator 16 may be made simply as one or more layers of a flexible and/or elastomeric polymer material and may include, as explained above, strengthening elements or a frame. The strengthening elements or frame may be self-expandable to assist in the initial expansion of the flow accelerator 16 within the patient following its release from the introducer assembly. A frame of this nature can be of spring or shape-memory material such as a shape-memory alloy, typically Nitinol.

It will be appreciated, particularly with regard to the embodiments of FIGS. 3, 4 and 6, that these could be delivered over the wire, that it is by means of a guide wire of the type often used for the endoluminal deployment of medical devices. In this regard, a guide wire can be passed through the structure of FIGS. 3, 4 and 6, that is across the one-way valves of the inflatable element 12 and through the flow accelerator 16, 56. The valves 42, 52 will be opened to allow the passage of the guide wire and will close once the guide wire has been removed from the plug.

Similar provision may be made with regard to the embodiments having only a single flow accelerator, that is the single-sided embodiments of FIGS. 1, 2 and 5. This can be achieved by providing an additional one-way valve in the inflatable element 12, similar to the one-way valve 42 of the embodiments of FIGS. 3, 4 and 6. The one-way valve in this circumstance could be opened to allow the passage of the guide wire through the inflatable element 12 but will close once the guide wire has been removed. The one-way valve would remain closed after the removal of the guide wire. The balloon wall at the one-way valve could be made material than the balloon wall at other locations of the balloon, in order to support a valve or the tubular element.

In other embodiments, the valve may be a self-sealing slit valve.

The embodiments of FIGS. 5 and 6 could be provided with external sleeves as in the embodiments of FIGS. 1, 2 and 4.

It is to be understood that the embodiments described above with reference to the accompanying drawings are only some of the embodiments of the invention and that others will be apparent to the person skilled in the art which will fall within the scope of the claims. It is to be appreciated also all of the features of the different embodiments described above may be combined with one another and are not exclusive of one another.

The invention claimed is:

1. A vascular plug for occluding a body vessel, the plug comprising:
   an inflatable element provided with an aperture;
   a flow accelerator including first and second ends, the first end providing a greater flow area than a flow area of the second end, the second end being coupled to the aperture of the inflatable element; and
   a sleeve disposed outside of and between the first end of the flow accelerator and the inflatable member.

2. A vascular plug according to claim 1, wherein the sleeve provides a fillable chamber.

3. A vascular plug according to claim 2, including one or more fluid outlets in the inflatable element coupling into the fillable chamber.

4. A vascular plug for occluding a body vessel, the plug comprising:
   an inflatable element provided with an aperture, and
   a flow accelerator including first and second ends, the first end providing a greater flow area than a flow area of the second end, the second end being coupled to the aperture of the inflatable element,
   the vascular plug including a generally conical fillable chamber around the flow accelerator.

5. A vascular plug according to claim 4, wherein the conical fillable chamber includes a closed conical membrane disposed radially outside of the flow accelerator.

6. A vascular plug for occluding a body vessel, the vascular plug comprising:
   an inflatable element provided with an aperture, and
   two flow accelerators each including first and second ends, each first end providing a greater flow area than a flow area of the second end of that flow accelerator, the two flow accelerators being in opposing relationship on either side of the inflatable member, the inflatable member including at least one aperture associated with and coupled to each of the flow accelerators.

7. A vascular plug according to claim 6, wherein the inflatable member includes a one-way valve at each aperture.

8. A vascular plug for occluding a body vessel, the plug comprising:
   an inflatable element provided with an aperture; and
   a flow accelerator including first and second ends, the first end providing a greater flow area than a flow area of the second end, the second end being coupled to the aperture of the inflatable element and providing a neck section, the neck section comprising a coil disposed therein.

9. A vascular plug according to claim 8, wherein the coil includes an internal coil surface providing a threaded coupling.

* * * * *